United States Patent
Kaser et al.

(12) 
(10) Patent No.: US 6,242,185 B1
(45) Date of Patent: Jun. 5, 2001

(54) PURIFIED NUCLEIC ACID ENCODING TRANSCRIPTION FACTOR REGULATORY PROTEIN

(75) Inventors: Matthew R. Kaser, Castro Valley; Mariah R. Baughn, San Leandro, both of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/286,132

(22) Filed: Apr. 1, 1999

(51) Int. Cl.[7] .............................. C12Q 1/68; C12N 1/00; C12N 5/10; C12N 15/12; C12N 15/63; C12P 21/02
(52) U.S. Cl. ............................ 435/6; 435/69.1; 435/243; 435/320.1; 435/325; 435/410; 536/23.5
(58) Field of Search .................................. 536/23.1, 23.5, 536/24.31; 435/320.1, 243, 410, 325, 69.1, 6

(56) References Cited

PUBLICATIONS

Chung, C. D., et al., *Specific Inhibition of Stat3 Signal Transduction by PIAS3, Science*, 278:1803–1805, (1997).

Puigserver, P., et al., *A Cold–Inducible Coactivator of Nuclear Receptors Linked to Adaptive Thermogenesis, Cell*, 92:829–839, (1998).

Heery, D.M., et al., *A signature motif in transcriptional co–activators mediates binding to nuclear receptors, Nature*, 387:733–736, (1997).

Moilanen, A., et al., *A Testis–specific Androgen Receptor Coregulator That Belongs to a Novel Family of Nuclear Proteins, J. Biol. Chem.*, 274:3700–3704, (1999).

Anzick, S.L, et al., *AIB1, a Steroid Receptor Coactivator Amplified in Breast and Ovarian Cancer, Science*, 277:965–968, (1997).

Chung, C.D., et al., (Direct Submission), GenBank Sequence Database (Accession AF0340801), National Center for Biotechnology Information, National Library of Medicine, Bethesda, Maryland, 20894 (GI 2689028).

Wible, B.A., et al., (Direct Submission), GenBank Sequence Database (Accession AF032872), National Center for Biotechnology Information, National Library of Medicine, Bethesda, Maryland, 20894 (GI 3127050).

*Primary Examiner*—Terry McKelvey
(74) *Attorney, Agent, or Firm*—Incyte, Genomics, Inc.

(57) ABSTRACT

The invention provides a mammalian nucleic acid sequence and fragments thereof. It also provides for the use of these nucleic acid sequences in a model system for the characterization, diagnosis, evaluation, treatment, or prevention of conditions, diseases and disorders associated with expression of the mammalian nucleic acid sequence. The invention additionally provides expression vectors and host cells for the production of the protein encoded by the mammalian nucleic acid sequence.

12 Claims, 10 Drawing Sheets

```
       10            19       28        37       46        55
5' GGAG AGT TGT GCG CCG GTC CCT GGG CCT GAG CTC CGG CTC CGG CGC CTG 64           73       82        91      100       109
   CGA TGT CTC AAG ATG GCG GAG CTG GGC GAA TTA AAG CAC ATG GTG ATG AGT TTC
                    M   A   E   L   G   E   L   K   H   M   V   M   S   F 118          127      136       145      154       163
   CGG GTG TCT GAG CTC CAG GTG CTT CTT GGC TTT GCT GGC CGG AAC AAG AGT GGA
    R   V   S   E   L   Q   V   L   L   G   F   A   G   R   N   K   S   G 172          181      190       199      208       217
   CGG AAG CAC GAG CTG CTG GCC AAG CTC CTG CAC CTG AAG TCC AGC TGT GCC
    R   K   H   E   L   L   A   K   L   L   H   L   K   S   S   C   A 226          235      244       253      262       271
   CCT AGT GTC CAG ATG AAG ATC AAA GAG CTT TAC CGA CGA CGC TTT CCC CGG AAG
    P   S   V   Q   M   K   I   K   E   L   Y   R   R   R   F   P   R   K 280          289      298       307      316       325
   ACC CTG GGG CCC TCT GAT CTC TCC CTT CTC TTG CCC CCC GGC ACC TCT CCT
    T   L   G   P   S   D   L   S   L   L   L   P   P   G   T   S   P 334          343      352       361      370       379
   GTA GGC TCC CCT GGT CCT CTA GCT CCC ATT CCC CCA ACG CTG TTG GCC CCT GGC
    V   G   S   P   G   P   L   A   P   I   P   P   T   L   L   A   P   G
```

FIGURE 1A

```
     388              397              406              415              424              433
ACC CTG GGC CCC  AAG CGT GAG GTG  GAC ATG CAC CCC  CCT CTG CCC CAG CCT
 T   L   G   P    K   R   E   V    D   M   H   P    P   L   P   Q   P 442              451              460              469              478              487
GTG CAC CCT GAT GTC  ACC ATG AAA CCA  TTG CCC TTC TAT  GAA GTC TAT GGG GAG
 V   H   P   D   V    T   M   K   P    L   P   F   Y    E   V   Y   G   E 496              505              514              523              532              541
CTC ATC CGG CCC ACC  ACC CTT GCA TCC  ACT TCT AGC CAG  CGG TTT GAG GAA GCG
 L   I   R   P   T    T   L   A   S    T   S   S   Q    R   F   E   E   A 550              559              568              577              586              595
CAC TTT ACC TTT GCC  CTC ACA CCC CAG  CAA GTG CAG CAG  ATT CTT ACA TCC AGA
 H   F   T   F   A    L   T   P   Q    Q   V   Q   Q    I   L   T   S   R 604              613              622              631              640              649
GAG GTT CTG CCA GGA GCC  AAA TGT GAT TAT  ACC ATA CAG GTG  CAG CTA AGG TTC
 E   V   L   P   G   A    K   C   D   Y    T   I   Q   V    Q   L   R   F 658              667              676              685              694              703
TGT CTC TGT GAG ACC AGC TGC CCC CAG GAA GAT TAT TTT CCC AAC CTC TTT
 C   L   C   E   T   S   C   P   Q   E   D   Y   F   P   N   L   F 712              721              730              739              748              757
GTC AAG GTC AAT GGG  AAA CTG TGC CCC  CTG CCG TAC CTT  CCG GGT TAC CTT  CCC CCA ACC AAG
 V   K   V   N   G    K   L   C   P    L   P   Y   L    P   G   Y   L    P   P   T   K
```

FIGURE 1B

```
         766          775          784          793          802          811
AAT GGG GCC GAG CCC AAG AGG CCC AGC CGC CCC ATC AAC ATC ACA CCC CTG GCT
 N   G   A   E   P   K   R   P   S   R   P   I   N   I   T   P   L   A 820          829          838          847          856          865
CGA CTC TCA GCC GTT CCC ACT GTT CCC AAC ACC ATT GTG GTC AAT TGG TCA TCT GAG TTC
 R   L   S   A   V   P   T   V   P   N   T   I   V   V   N   W   S   S   E   F 874          883          892          901          910          919
GGA CGG AAT TAC TCC TTG TCT GTG TAC CTG GTG AGG CAG TTG ACT GCA GGA ACC
 G   R   N   Y   S   L   S   V   Y   L   V   R   Q   L   T   A   G   T 928          937          946          955          964          973
CTT CTA CAA AAA CTC AGA GCA AAG GGT ATC CGG AAC CCA GAC CAC TCG CGG GCA
 L   L   Q   K   L   R   A   K   G   I   R   N   P   D   H   S   R   A 982          991         1000         1009         1018         1027
CTG ATC AAG GAG AAA TTG ACT GCT GAC CCT GAC AGT GAG GTG GCC ACT ACA AGT
 L   I   K   E   K   L   T   A   D   P   D   S   E   V   A   T   T   S 1036         1045         1054         1063         1072         1081
CTC CGG GTG TCA CTC ATG TGC CCG CTA GGG AAG ATG CGC CTG ACT GTC CCT TGT
 L   R   V   S   L   M   C   P   L   G   K   M   R   L   T   V   P   C 1090         1099         1108         1117         1126         1135
CGT GCC CTC ACC TGC GCC CAC CTG CAG AGC TTC GAT GCT GCC CTT TAT CTA CAG
 R   A   L   T   C   A   H   L   Q   S   F   D   A   A   L   Y   L   Q
```

FIGURE 1C

```
        1144        1153        1162        1171        1180        1189
ATG AAT GAG AAG AAG CCT ACA TGG ACA TGT CCT GTG TGT GAC AAG AAG GCT CCC
 M   N   E   K   K   P   T   W   T   C   P   V   C   D   K   K   A   P 1198        1207        1216        1225        1234        1243
TAT GAA TCT CTT ATC ATT GAT GGT TTA TTT ATG GAG ATT CTT AGT TCC TGT TCA
 Y   E   S   L   I   I   D   G   L   F   M   E   I   L   S   S   C   S 1252        1261        1270        1279        1288        1297
GAT TGT GAT GAG ATC CAA TTC ATG GAA GAT GGA TCC TGG TGC CCA ATG AAA CCC
 D   C   D   E   I   Q   F   M   E   D   G   S   W   C   P   M   K   P 1306        1315        1324        1333        1342        1351
AAG GAG GCA TCT GAG GTT TGC CCC CCG CCA CCA TCA GGG TAT GGG CTG GAT GGC CTC
 K   E   A   S   E   V   C   P   P   P   P   S   G   Y   G   L   D   G   L 1360        1369        1378        1387        1396        1405
CAG TAC AGC CCA GTC CAG GGG GGA GAT CCA TCA GAT GAG AAT AAG AAG AAG GTC GAA
 Q   Y   S   P   V   Q   G   G   D   P   S   D   E   N   K   K   K   V   E 1414        1423        1432        1441        1450        1459
GTT ATT GAC TTG ACA ATA GAA AGC TCA TCA GAT GAG GAG GAT CTG CCC CCT ACC
 V   I   D   L   T   I   E   S   S   S   D   E   E   D   L   P   P   T 1468        1477        1486        1495        1504        1513
AAG AAG CAC TGT TCT ACC GTC ACC TCA GCT GCC ATC CCG GCC CTA CCT GGA AGC AAA
 K   K   H   C   S   T   V   T   S   A   A   I   P   A   L   P   G   S   K
```

FIGURE 1D

```
       1522        1531        1540        1549        1558        1567
GGA GTC CTG ACA TCT GGC CAC CAG CCA TCC TCG GTG CTA AGG AGC CCT GCT ATG
 G   V   L   T   S   G   H   Q   P   S   S   V   L   R   S   P   A   M 1576        1585        1594        1603        1612        1621
GGC ACG TTG GGT GGG GAT TTC CTG TCC AGT CTC CCA CTA CAT GAG TAC CCA CCT
 G   T   L   G   G   D   F   L   S   S   L   P   L   H   E   Y   P   P 1630        1639        1648        1657        1666        1675
GCC TTC CCA CTG GGA GCC GAC ATC CAA GGT TTA GAT CTA TTT TCA TTT CTT CAG
 A   F   P   L   G   A   D   I   Q   G   L   D   L   F   S   F   L   Q 1684        1693        1702        1711        1720        1729
ACA GAG AGT CAG CAC TAT GGC CCC TCT GTC ATC ACC TCA CTA GAT GAA CAG GAT
 T   E   S   Q   H   Y   G   P   S   V   I   T   S   L   D   E   Q   D 1738        1747        1756        1765        1774        1783
GCC CTT GGC CAC TTC CAG TAC CGA GGG ACC CCT TCT CAC TTT CTG GGC CCA
 A   L   G   H   F   Q   Y   R   G   T   P   S   H   F   L   G   P 1792        1801        1810        1819        1828        1837
CTG GCC CCC ACG CTG GGG AGC TCC AGC TGC AGC CCG ACT CCG GCG CCC CCT CCT
 L   A   P   T   L   G   S   S   S   C   S   A   T   P   A   P   P   P 1846        1855        1864        1873        1882        1891
GGC CGT GTC AGC AGC ATT GTG GCC CCT GGG GGG CTT GAG GGG CAT GGA
 G   R   V   S   S   I   V   A   P   G   G   A   L   R   E   G   H   G
```

FIGURE 1E

```
            1900      1909      1918      1927      1936      1945
GGA CCC CTG CCC TCA GGT CCC TCT TTG ACT GGC TGT CGG TCA GAC ATC ATT TCC
 G   P   L   P   S   G   P   S   L   T   G   C   R   S   D   I   I   S 1954      1963      1972      1981      1990      1999
CTG GAC TGA GTT CCC TGG ATT ATG GAA ACT TCG CTG TCC CCC AAC ACT GAG CAA
 L   D 2008      2017      2026      2035      2044      2053
GTA TGC TGT GGA GTC CCA ACC CCA GCT ACT CTG ATC CCT CTG GGG GCT CTG GCC 2062      2071      2080      2089      2098      2107
AAG GGC CAG ACA GAC CTT CAC AGA TGC CTA CTT TTG GCC TCA TCT CTG CCT GAC 2116      2125      2134      2143      2152      2161
AAG GCC AGC ACC CAA AGG GTT AAT ATT TAA CCT CTT TTT TAA GGA CAC TGG GGT 2170      2179      2188      2197      2206      2215
CTG TCT CCT GGA ATG TTC TTT AGA TGG TGG CAC ATT CCT TTG NGG TAT GTT AAC 2224      2233      2242      2251      2260
CTA GGC ACT GGG ANG CAA ATG GGG ATT GTA TGT GAG CTA GGA GAA GG 3'
```

| | | |
|---|---|---|
| 357 | M N E K K P T W T C P V C D K K A P Y E S L I I D G L F M E | 2667068 |
| 312 | M N E K K P T W T C P V C D K K A P Y E S L I I D G L F M E | GI 2689028 |

| | | |
|---|---|---|
| 387 | I L S S C S D C D E I Q F M E D G S W C P M K P K K E A S E | 2667068 |
| 342 | I L N S C S D C D E I Q F M E D G S W C P M K P K K E A S E | GI 2689028 |

| | | |
|---|---|---|
| 417 | V C P P P G Y G L D G L Q Y S P V Q G G D P S E N K K V E | 2667068 |
| 372 | V C P P P G Y G L D G L Q Y S A V Q E G I Q P E S K K R V E | GI 2689028 |

| | | |
|---|---|---|
| 447 | V I D L T I E S S D E E D L P P T K K H C S V T S A A I P | 2667068 |
| 402 | V I D L T I E S S D E E D L P P T K K H C P V T S A A I P | GI 2689028 |

| | | |
|---|---|---|
| 477 | A L P G S K G V L T S G H Q P S S V L R S P A M G T L G G D | 2667068 |
| 432 | A L P G S K G A L T S G H Q P S S V L R S P A M G T L G S D | GI 2689028 |

| | | |
|---|---|---|
| 507 | F L S S L P L H E Y P P A F P L G A D I Q G L D L F S F L Q | 2667068 |
| 462 | F L S S L P V H E Y P P A F P L G A D I Q G L D L F S F L Q | GI 2689028 |

PURIFIED NUCLEIC ACID ENCODING TRANSCRIPTION FACTOR REGULATORY PROTEIN

FIELD OF THE INVENTION

This invention relates to nucleic acid and amino acid sequences of a new mammalian protein and to the use of these sequences in the characterization, diagnosis, prevention, and treatment of cell proliferative disorders.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Signal transduction cascades alter gene expression by activation or suppression of transcription factor activity. Two basic types of transcription factors exist within the cell. Steroid hormone receptors are transcription factors whose activity is regulated by binding to lipid soluble hormones, such as steroids, retinoids, and thyroid hormones. Nuclear receptors are transcription factors, such as CREB (cAMP-response element binding protein), STAT (Signal Transducers and Activators of Transcription),and the TCF (ternary complex factor)-SRF (serum-response factor) complex, whose activity is regulated by phosphorylation cycles. The kinases and phosphatases that regulate the phosphorylation cycle respond to extracellular signals, such as growth factors and cytokines.

Hormone binding or phosphorylation induce conformational changes in transcription factors which promote their association with a diverse group of nuclear transcription factor binding proteins (TFBPs) including steroid receptor co-activator (SRC)-1, transcriptional intermediary factor (TIF), and CREB binding protein (CBP)/p300. These TFBPs function as modulators of transcription and show specificity towards transcription factor and associated ligands. For example, PIAS (protein inhibitor of activated STAT)-3 preferentially binds phosphorylated Stat3. Furthermore, IL-6 but not interferon-γ stimulates interaction between Stat3 and PIAS3 (Chung et al. (1997) Science 278:1803–1805). Many TFBPs also have a restricted tissue distribution. For example, β-3 adrenergic agonists activate peroxisome proliferator-activated receptor (PPAR)-γ. PPARγ is a major regulator of fat cell-specific gene regulation and differentiation, but does not inherently distinguish whether fat cells proceed along energy storage (white fat) or energy dissipation (brown fat) pathways. PGC-1, a modulator of PPARγ, is found only in brown fat and leads to specific activation of genes associated with energy dissipating adaptive thermogenesis (Puigserver et al. (1998) Cell 92:829–839).

A short sequence motif LXXLL is necessary and sufficient to mediate binding of TFBPs to activated nuclear receptors (Heery et al. (1997) Nature 387:733–736). The motif forms an α-helix and occurs at the boundary of nuclear receptor interaction domains. ARIP3, which contains two LXXLL motifs, is an androgen receptor binding protein expressed predominantly in the testis which provides tissue specific gene activation by androgens (Moilanen et al. (1999) J. Biol. Chem. 274:3700–3704). ARIP3 is a member of a family of related TFBPs which include the PIAS proteins and Gu/RNA helicase II-binding protein (GBP). These proteins show 60–80% homology over the N-terminal and central regions of the proteins, but contain divergent C-termini. All of the PIAS family members also contain a potential zinc finger motif which is involved in transcription factor binding.

TFBPs, by binding and modulating transcription factor activity in a signal and tissue specific manner, provide additional regulation to cell signaling events. Inappropriate expression or activation of TFBPs can alter gene expression patterns and cell fates. AIB (amplified in breast cancer)-1, a member of the SRC1 family, interacts with the estrogen receptor and enhances estrogen receptor-dependent gene transcription. It is ubiquitously expressed in normal human tissues and is amplified and overexpressed in many breast and ovarian cancer cell lines and in breast cancer tumor samples (Anzick et al. (1997) Science 277:965–968). Mice lacking brown fat develop severe obesity and insulin resistance. Chronic exposure to β-3 adrenergic agonists cause brown fat hypertrophy and thermogenic, anti-obesity effects due to enhanced activity of PGC1-PPARγ (Puigserver, supra).

The discovery of a polynucleotide encoding a new mammalian protein satisfies a need in the art by providing new compositions which are useful in the characterization, diagnosis, prevention, and treatment of cell proliferative disorders.

SUMMARY OF THE INVENTION

The invention is based on the discovery of a polynucleotide encoding a mammalian protein (TFRP) which satisfies a need in the art by providing new compositions useful in the characterization, diagnosis, prevention, and treatment of cell proliferative disorders.

The invention provides an isolated and purified mammalian polynucleotide comprising the nucleic acid sequence of SEQ ID NO:1 or a fragment thereof. The invention also provides fragments homologous to the mammalian polynucleotide from rat, mouse, and monkey.

The invention further provides an isolated and purified polynucleotide or a fragment thereof which hybridizes under high stringency to the polynucleotide encoding the polypeptide. The invention also provides an isolated and purified polynucleotide or a fragment thereof having a nucleic acid sequence which is complementary to the polynucleotide encoding the polypeptide.

The invention further provides a method for detecting a polynucleotide in a sample containing nucleic acids, the method comprising the steps of: (a) hybridizing the complement of the polynucleotide sequence to at least one of the nucleic acids of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization. The polynucleotide or fragment thereof may comprise an element or target on a microarray. The invention also provides a method for screening a plurality of molecules for specific binding to a polynucleotide or a fragment thereof, the method comprising providing a plurality of molecules, combining the polynucleotide of claim 1 with a plurality of molecules under conditions suitable to allow specific binding, and detecting binding of the polynucleotide to each of a plurality of molecules, thereby identifying at least one molecule which specifically binds the polynucleotide. Such molecules are potential regulators of polynucleotide function.

The invention also provides an expression vector containing at least a fragment of the polynucleotide of SEQ ID NO:1. In another aspect, the expression vector is contained within a host cell. The invention further provides a method for producing a polypeptide, the method comprising the steps of culturing the host cell under conditions suitable for the expression of the polypeptide and recovering the polypeptide from the host cell culture. The invention also provides an isolated and purified polypeptide comprising the amino acid sequence of SEQ ID NO:2 or a portion thereof. Additionally, the invention provides a pharmaceutical composition comprising a substantially purified polypeptide having the sequence of SEQ ID NO:2 or a portion thereof in conjunction with a suitable pharmaceutical carrier.

The invention further provides a method for using a portion of the polypeptide to produce antibodies. The invention also provides a method for using a polypeptide or a portion thereof to screen for molecules which specifically bind the polypeptide, the method comprising the steps of combining the polypeptide or a portion thereof with a plurality of molecules under conditions suitable to allow complex formation and detecting complex formation, wherein the presence of the complex identifies a molecule which specifically binds the polypeptide. In one aspect, a molecule identified using the method increases the activity of the polypeptide. In another aspect, a molecule identified using the method decreases the activity of the polypeptide.

BRIEF DESCRIPTION OF THE FIGURES AND TABLE

FIGS. 1A, 1B, 1C, 1D, 1E, and 1F show the nucleic acid sequence (SEQ ID NO:1) encoding the amino acid sequence (SEQ ID NO:2) of the mammalian protein. The alignment was produced using MACDNASIS PRO software (Hitachi Software Engineering, South San Francisco Calif).

FIGS. 2A, 2B, 2C, and 2D show the chemical and structural similarity between SEQ ID NO:2 and PIAS3 (GI 2689028; SEQ ID NO:17). The amino acids of SEQ ID NO:2, from residue 88 to residue 105, are appropriate for antibody production.

Table 1 shows the ESTs from human, rat, mouse, and monkey which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"TFRP" refers to a substantially purified protein obtained from any mammalian species, including murine, bovine, ovine, porcine, simian, and preferably the human species, and from any source, whether natural, synthetic, semi-synthetic, or recombinant.

"Agents, molecules, or compounds" are used substantially interchangably and refer to that which interacts with, specifically binds to, or modifies the polynucleotides and proteins of the invention; and may be composed of at least one of the following: nucleic acids, proteins, carbohydrates, fats, lipids, organic and inorganic substances.

"Biologically active" refers to a protein having structural, immunological, regulatory, or chemical functions of a naturally occurring, recombinant or synthetic molecule.

"Complementary" refer to the natural base pairing by hydrogen bonding between purines and pyrimidines. For example, the sequence A-C-G-T forms hydrogen bonds with its complement T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a polynucleotide or polypeptide sequence. Chemical modifications of a sequence can include replacement of hydrogen by an alkyl, acyl, or amino group or glycosylation, pegylation, or any similar process which retains or enhances biological activity or lifespan of the molecule.

"Fragment" refers to an Incyte clone or any part of a polynucleotide which retains a usable, functional characteristic. Useful fragments include oligonucleotides which may be used in hybridization or amplification technologies or in regulation of replication, transcription or translation.

"Hybridization complex" refers to a complex between two nucleid acid sequences by virtue of the formation of hydrogen bonds between purines and pyrimidines.

"Polynucleotide" refers to a nucleic acid, nucleic acid sequence, oligonucleotide, nucleotide, or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Polypeptide" refers to an amino acid, amino acid sequence, oligopeptide, peptide, or protein or portions thereof whether naturally occurring or synthetic.

"Portion", as used herein, refers to any part of a protein used for any purpose, but especially for the screening of molecules or compounds which specifically bind to that part or for the production of antibodies.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

Molecules or compounds which "specifically bind" the mammalian polynucleotide or polypeptide may include, nucleic acids, carbohydrates, lipids, proteins, or any other organic or inorganic molecules or their combinations which stabilize, increase, or decrease the activity of the mammalian protein.

"Substantially purified" refers to nucleic acid or amino acid sequences that are removed from their natural environment and are isolated or separated, and are at least about 60% free, preferably about 75% free, and most preferably about 90% free, from other components with which they are naturally associated.

"Substrate" refers to any suitable rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

The Invention

The invention is based on the discovery of a new mammalian polynucleotide which encodes a mammalian protein (TFRP) and the use of the nucleic acid sequence, or fragments thereof, and amino acid sequences, or portions thereof, as compositions in the characterization, diagnosis, treatment, or prevention of cell proliferative disorders.

Nucleic acids encoding the mammalian protein of the present invention were identified by BLAST against Incyte clone 700706487. A consensus sequence, SEQ ID NO:1, was assembled from the following overlapping and/or extended nucleic acid fragments found in Incyte Clones 1416935F6 and 1412996F6, 2481857F6, 2667068H1, 3550644H1, SBFA02969F1, and 1666914F6; SEQ ID NOs: 3–9,respectively. FIGS. 1A, 1B, 1C, 1D, 1E, and 1F, show the deduced translation of SEQ ID NO:1.

In one embodiment, the protein comprising the amino acid sequence of SEQ ID NO:2, TFRP, is 628 amino acids in length and has three potential N-glycosylation sites at residues N29, N261, and N269; two potential cAMP- and cGMP-dependent protein kinase phosphorylation sites at residues S239 and T363; eight potential casein kinase II phosphorylation sites at residues T174, S390, S392, S454, S455, S456, T548, and S549; and seven potential protein kinase C phosphorylation sites at residues S13, S31, T128, S152, T174, S320, and T464. TFRP has two LXXLL motifs from residue L19 through L23 and L285 through L289; one LXXII motif from residue 380 through 384; and a potential zinc finger motif from residue C366 through C394. The LXXLL and LXXII motifs have an α-helical structure as predicted by MACDNASIS PRO software (Hitachi Software Engineering). As shown in FIGS. 2A, 2B, 2C, and 2D, the protein has chemical and structural similarity with mouse PIAS3 (GI2689028; SEQ ID NO:17). In particular, TFRP and PIAS3 share 82% identity. Also, TFRP and PIAS3 share the LXXLL motifs (residues 10 through 14 and 240 through 244 in PIAS3), LXXII motif (residues 334 through 338 in PIAS3), and zinc finger motif (residues 321 through 349 in PIAS3).

Table 1 shows the nucleic acid fragments from human, rat, mouse, and monkey and their sequence coverage and identity with SEQ ID NO:1. Columns 1 and 2 list the SEQ ID NO and Incyte clone number, respectively, for each nucleic acid fragment. The fragments of SEQ ID NO:1, SEQ ID NOs:3–9, are useful in hybridization or amplification technologies to identify and distinguish between the mammalian sequences disclosed herein and similar sequences. Column 3 lists the nucleotide length for each fragment. Columns 4 and 5 identify the source organism and Incyte cDNA library from which the fragments were isolated. Column 6 identifies the range of nucleotide residues in SEQ ID NO:1 over which each fragment shows identity. Column 7 shows the sequence identity between each fragment and SEQ ID NO:1 over the range defined in column 6.

Northern analysis shows the expression of TFRP in various libraries, particularly in endothelial and nervous tissues of human, rat, mouse, and monkey. Of particular note is the expression of TFRP in conditions, such as cancer, associated with cell proliferation.

The mammalian fragments comprising SEQ ID NO:10–13 from rat, SEQ ID NO:14 from mouse, and SEQ ID NO:15–16 from monkey were identified using either SEQ ID NO:1 or SEQ ID NOs:3–9. These fragments may be used to obtain the full length sequence for a particular species which in turn can be used to produce transgenic animals which mimic human diseases. The fragments are useful in hybridization and amplication technologies to monitor animal toxicological studies, clinical trials, and subject/patient treatment profiles through time.

Characterization and Use of the Invention

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequence was chemically and/or electronically assembled from fragments including Incyte clones, extension, and/or shotgun sequences using computer programs such as the AUTOASSEMBLER application (P.E. Biosystems, Foster City Calif.).

Methods for sequencing nucleic acids are well known in the art and may be used to practice any of the embodiments of the invention. These methods employ enzymes such as the Klenow fragment of DNA polymerase I, SEQUENASE, Taq DNA polymerase, and thermostable T7 DNA polymerase (Amersham Pharmacia Biotech, Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (Perkin-Elmer), the MEGABACE 1000 DNA sequencing system (Amersham Pharmacia Biotech), and the like. The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative of regions flanking the nucleic acid sequences of interest.

Prefinished sequences (incomplete assembled sequences) are inspected for identity using various algorithms or programs well known in the art, such as CONSED (Gordon (1998) Genome Res. 8:195–202). Contaminating sequences including vector or chimeric sequences or deleted sequences can be removed or restored, respectively, organizing the prefinished sequences into finished sequences.

The sequences of the invention may be extended using various PCR-based methods known in the art. For example, the XL-PCR kit (P.E.Biosystems), nested primers, and commercially available cDNA or genomic DNA libraries (Life Technologies; Clontech, Palo Alto Calif., respectively) may be used to extend the nucleotide sequence. For all PCR-based methods, primers may be designed using commercially available software, such as OLIGO 4.06 Primer Analysis software (National Biosciences, Plymouth Minn.) to be about 22 to 30 nucleotides in length, to have a GC content of about 50% or more, and to anneal to a target sequence at temperatures of about 68° C. to 72° C. When extending a sequence to recover regulatory elements, it is preferable to use genomic, rather than cDNA libraries.

The polynucleotide sequence of SEQ ID NO:1 and fragments thereof can be used in various hybridization technologies for various purposes. Hybridization probes may be designed or derived from SEQ ID NO:1. Such probes may be made from a highly specific region such as the 5' regulatory region or from a conserved motif, an used in protocols to identify naturally occurring sequences encoding the mammalian protein, allelic variants, or related sequences, and should preferably have at least 50% sequence identity to any of the protein sequences. The hybridization probes of the subject invention may be DNA or RNA and may be derived from the sequence of SEQ ID NO:1 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an appropriate RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, additions of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as salmon sperm DNA. Selection of components and conditions for hybridization are well known to those skilled in the art and are reviewed in Ausubel (supra) and Sambrook et al. (1989) *Molecular Cloning, A Laboratory Manual,* Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO95/251116; Shalon et al. (1995) PCT application WO95/35505; Heller et al. (1997) Proc. Natl. Acad. Sci. 94:2150–2155; and Heller et al. (1997) U.S. Pat. No. 5,605,662.)

Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

A multitude of polynucleotide sequences capable of encoding the mammalian protein may be cloned into a vector and used to express the protein, or portions thereof, in appropriate host cells. The nucleotide sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain appropriate transcriptional and translational control elements (promoters, enhancers, specific initiation signals, and 3' untranslated regions) from various sources which have been selected for their efficiency in a particular host. The vector, nucleic acid sequence, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an appropriate expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. Sequences may be ligated into the non-essential E1 or E3 region of the viral genome, and the infective virus used to transform and express the protein in host cells. The Rous sarcoma virus enhancer or SV40 or EBV-based vectors may also be used for high-level protein expression Routine cloning, subcloning, and propagation of polynucleotide sequences can be achieved using the multifunctional PBLUESCRIPT vector (Stratagene, La Jolla Calif.) or PSPORT1 plasmid (Life Technologies). Introduction of a polynucleotide sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β0 glucuronidase, luciferase and the like, may be propagated using appropriate tissue culture techniques. Visible markers are also used to quantify the amount of protein expressed by the introduced genes. Verification that the host cell contains the desired mammalian polynucleotide is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells which have specific cellular machinery and characteristic mechanisms for post-translational activities (CHO, HEK293, and WI38; American Type Culture Collection (ATCC), Bethesda Md.) may be chosen to ensure the correct modification and processing of the foreign protein.

Heterologous moieties engineered into a vector for ease of purification include glutathione S-transferase (GST), calmodulin binding peptide (CBF), 6His, FLAG, c-myc, and the like. GST, CBP, and 6-His are purified using commercially available affinity matrices such as immobilized glutathione, calmodulin, and metal-chelate resins, respectively. FLAG, and c-myc, are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the ABI 431A Peptide synthesizer (P.E. Biosystems). A protein or portion thereof may be substantially purified by preparative high performance liquid chromatography and its composition confirmed by amino acid analysis or by sequencing (Creighton (1984) *Proteins, Structures and Molecular Properties,* WH Freeman, New York N.Y.).

Various hosts including goats, rabbits, rats, mice, humans, and others may be immunized by injection with mammalian protein or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope-specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols,* Humana Press, Totowa N.J.).

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a abeled nucleotide such as $^{32}$P-dCTP, Cy3-dCTP or Cy5-dCTP (Amersham Pharmacia Biotech) or amino acid such as $^{35}$S-methionine a Persham Pharmacia Biotech. Nucleic acids and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The polynucleotides, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Condition, diseases or disorders associated with altered expression of TFRP include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleotide sequence may be labeled by standard methods and added to a biological sample from a patient under conditions suitable for the formation of hybridization complexes. After a suitable incubation period, the sample is washed and the amount of label, or its signal, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a sequence or a fragment thereof under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to rmine if the level of expression in the patient begins to approximate that which is observed in a normal subject. The results obtained from successive assays may be used to show the efficacy of treatment over a period ranging from several days to months.

Therapeutics

Chemical and structural similarity, e.g., in the context of sequences and motifs, exists between regions of the mammalian TFRP and mouse PIAS3. In addition, expression is closely associated with endothelial and nervous tissues and appears to play a role in cell proliferative disorders. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising a substantially purified the mammalian protein in conjunction with a suitable pharmaceutical carrier may be administered to a subject to treat or prevent a condition associated with altered expression or activity of the mammalian protein including, but not limited to, those provided above.

In a further embodiment, an agonist which modulates the activity of the mammalian protein may be administered to a subject to treat or prevent a condition associated with altered expression or activity of the protein including, but not limited to, those listed above.

In an additional embodiment, a vector capable of expressing the mammalian protein or a portion or derivative thereof may be administered to a subject to treat or prevent a condition associated with altered expression or activity of protein including, but not limited to, those described above.

In yet another embodiment, an antagonist or inhibitor of the mammalian protein may be administered to a subject to treat or prevent a condition associated with altered expression or activity of the protein. In one aspect, an antibody which specifically binds the mammalian protein may be used directly as an antagonist or indirectly as a targeting or delivery mechanism for bringing a pharmaceutical agent to cells or tissue which express the mammalian protein.

In a still further embodiment, a vector expressing the complement of the polynucleotide encoding the mammalian protein may be administered to a subject to treat or prevent a condition associated with altered expression or activity of the protein including, but not limited to, those described above.

Any of the nucleic acids, complementary sequences, vectors, proteins, agonists, antagonists, or antibodies of the invention may be administered in combination with other appropriate therapeutic agents. Selection of the appropriate agents for use in combination therapy may be made by one of ordinary skill in the art according to conventional pharmaceutical principles. A combination of therapeutic agents may act synergistically to effect prevention or treatment of a particular condition at a lower dosage of each agent.

Gene expression may be modified by designing complementary sequences or antisense molecules (DNA, RNA, or PNA) to the control, 5', or regulatory regions of the gene encoding the mammalian protein. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches,* Futura Publishing, Mt. Kisco N.Y., pp. 163–177.) A complementary sequence may also be designed to block translation by preventing binding between ribosomes and mRNA.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

The nucleic acid sequence encoding the mammalian protein may be used to screen a library of molecules for specific binding affinity. The assay can be used to screen a library of DNA molecules, RNA molecules, PNAs, peptides, or proteins including transcription factors, enhancers, repressors, and the like which regulate the activity of the nucleic acid sequence in the biological system. The assay involves providing a library molecules, combining the mammalian nuc acid sequence or a fragment thereof with the library of molecules under conditions suitable to allow specific binding, and detecting specific binding to identify at least one molecule which specifically binds the nucleic acid sequence.

Similarly the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs and the like, which specifically bind the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a toxic response similar to that of humans and where exposure conditions are relevant to human exposures. Mammals are the most common models and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A rodent strain inbred to over-express a particular gene may also serve as a convenient source of the protein expressed by that gene.

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Toxicological tests measure the effects of a single, repeated, or long-term exposure of a subject to an agent. Agents may be tested for specific endpoints such as cytotoxicity, mutagenicity, carcinogenicity and teratogenicity. Degree of response varies according to the route of exposure (contact, ingestion, injection, or inhalation), age, sex, genetic makeup, and health status of the subject. Toxicokinetic studies trace the absorption, distribution, metabolism, storage, and excretion of the agent in subject tissues, and toxicodynamic studies chart biological responses that are consequences of the presence of the agent in subject tissues.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle and their capacity to be raised in numbers sufficient to satisfy statistical requirements.

All toxicology studies on experimental animals involve the preparation of a suitable form of the agent for administration, the selection of the route of administration, and the selection of the species to resemble the species of pharmacological interest. Dose concentrations are varied to investigate a range of dose-related effects which are identified, measured, and related to exposure.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic rodents which over-express or under-express a gene of interest may be inbred and used to model human diseases or to test therapeutic or toxic agents. (See, e.g., van Beusechem and Valerio In: Murray (1 992) *Transgenesis: Applications of Gene Transfer,* John Wiley & Sons Ltd. Chichester, England, pp. 283–289.) To produce the rat or mouse model, a gene candidate which mimics a human disease is coupled to a strong promoter and injected into a fertilized egg, and the egg transferred into a pseudopregnant dam. The promoter may be activated at a specific time in a specific tissue type during fetal development or postnatally. Expression of the transgene is monitored by analysis of phenotype, tissue-specific mRNA expression, and challenged with experimental drug therapies. Examples of transgenes used as models of human disease include the investigation of the mutant amyloid precursor protein and apolipoprotein E genes in familial Alzheimer's Disease (Price and Sisodia (1998) Annu. Rev. Neurosci. 21:479–505).

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene sequence which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected under appropriate conditions, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang etal. (1998) Mol. Cell Biol. 18:3340–3349).

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macacafascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as "extensive metabolizers" and "poor metabolizers" of these agents. For this reason, NHPs are the favored models for studying metabolism and toxicology of agents acted upon by the cytochrome $P_{450}$ family of enzymes.

In additional embodiments, the nucleotide sequences which encode the mammalian protein may be used in any molecular biology techniques that have yet to be developed, provided the new techniques rely on properties of nucleotide sequences that are currently known, including, but not limited to, such properties as the triplet genetic code and specific base pair interactions.

Examples

I Representative cDNA sequence preparation

The monkey prefrontal cortex cDNA library MNBFNOT01 was constructed from dorsal prefrontal cortex tissue microdissected from the brain of a Cynomolgus (Old World) monkey. The frozen tissue was homogenized and lysed in TRIZOL reagent (0.8 g tissue/12 ml TRIZOL; Life Technologies), a monophasic solution of phenol and guanidine isothiocyanate, using an POLYTRON homogenizer (PT-3000; Brinkmann Instruments, Westbury N.Y.). The homogenate was centrifuged, and the supernatant was decanted into a fresh tube and incubated briefly at 15–30° C. After chloroform was added (1:5 v/v chloroform:homogenate), the mixture was shaken vigorously by hand and incubated briefly at 15–30° C. The phases were separated by centrifugation, and the aqueous phase was removed to a fresh tube, mixed with isopropanol, and centrifuged. The RNA pellet was washed twice with 75% ethanol, resuspended in 0.3M sodium acetate and 2.5 volumes 100% ethanol, and centrifuged. The RNA was dissolved in DEPC-treated water and treated with DNaseI (Life Technologies) for 45 minutes at 25° C. The RNA was re-extracted with phenol-chloroform-isoamyl alcohol, and precipitated with 0.5 M ammonium acetate and 2.5 volumes 100% ethanol, centrifuged, washed twice with 75% ethanol, and resuspended in DEPC-treated water.

Messenger RNA (mRNA) was isolated using the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL-4B column (Amersham Pharmacia Biotech), and those cDNAs exceeding 400 bp were ligated into the NotI and EcoRI sites of the pINCY 1 plasmid (Incyte Pharmaceuticals, Palo Alto Calif.). The plasmid was transformed into competent DH5α cells (Life Technologies) or ELECTROMAX DH10B cells (Life Technologies).

Plasmid DNA was released from the cells and purified using the REAL Prep 96 plasmid kit (Qiagen). This kit enabled simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cultures were incubated for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using either a MICROLAB 2200 system (Hamilton, Reno Nev.) or a HYDRA microdispenser (Robbins Scientific, Sunnyvale Calif.) in combination with the DNA ENGINE thermal cyclers (MJ Research) and sequenced by the method of Sanger, F. and A.R. Coulson (1975; J. Mol. Biol. 94:441–448) using an ABI PRISM 377 sequencing system (PE Biosystems). Most of the isolates were sequenced according to standard ABI protocols and kits (Cat.#79345, 79339, 79340, 79357, and 79355; PE Biosystems). The solution volumes were used at 0.25×–1.0× concentrations. In the alternative, cDNAs were sequenced using solutions and dyes from Amersham Pharmacia Biotech.

II Identification, Extension, Assembly, and Analyses of the Sequences

Incyte clone 700706487 from ZOOSEQ database (Incyte Pharmaceuticals, Palo Alto Calif.) was used to identify Incyte Clone 2667068 from the LIFESEQ database (Incyte Pharmaceuticals). The first pass and extended cDNAs, SEQ ID NOs:3–9, which cluster with Incyte clone 2667068 were assembled using Phred/Phrap or CONSED (Green, University of Washington), GCG Fragment assembly system (Genetics Computer Group, Madison Wis.). The assembled sequence was searched for open reading frames using GENEMARK (source) or MACDNASIS PRO software (Hitachi Software Engineering), and the coding region was translated using MACDNASIS PRO software. The full length nucleotide and amino acid sequences were analyzed by BLAST queries against databases such as the GenBank databases, SwissProt, BLOCKS, PRINTS, Prosite, and PFAM and by LASERGENE software (DNASTAR). Functional analyses of the amino acid sequences were performed using Motifs (source) and HMM algorithms. Antigenic index (Jameson-Wolf analysis) of the amino acid sequences were determined using LASERGENE software (DNASTAR). Then, the clones and assembled sequence were compared using BLAST across all mammalian libraries to identify homologous nucleic acid sequences, SEQ ID NOs:10–15.

III Sequence Similarity

Sequence similarity was calculated as percent identity based on comparisons between at least two nucleic acid or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled nucleotide sequence to a membrane on which RNAs from a particular cell type or tissue have been bound.

Analogous computer techniques applying BLAST were used to search for identical or related molecules in nucleotide databases such as GenBank or LIFESEQ (Incyte Pharmaceuticals). Sequence-based analysis is much faster than membrane-based hybridization, and the sensitivity of the computer search can be modified to determine whether any particular match is categorized as exact or similar. The basis of the search is the product score which is defined as: (percent sequence identity×percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Polynucleotides

The nucleic acid sequence of SEQ ID NO:1 was produced by extension of Incyte cDNA clones using oligonucleotide primers. One primer was synthesized to initiate 5' extension of the known fragment, and the other, to initiate 3' extension of the known fragment. The initial primers were designed using OLIGO 4.06 software (National Biosciences) to be about 22 to 30 nucleotides in length, to have a GC content of about 50%, and to anneal to the target sequence at temperatures of about 68° C. to about 72° C. Any fragment which would result in hairpin structures and primer-primer dimerizations was avoided. Selected human cDNA libraries were used to extend the sequence. If more than one extension was necessary or desired, additional or nested sets of primers were designed.

High fidelity amplification was obtained by performing PCR in 96-well plates using the PTC-200 (MJ Research). The reaction mix contained DNA template, 200 nmol of each primer, reaction buffer containing $Mg^{2+}$, $(NH_4)_2SO_4$, and β-mercaptoethanol, TAQ DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15sec; Step 3: 60° C., 1 min; Step 4: 68° C., 2 min; Step 5: Steps 2, 3, and 4 repeated 20 times; Step 6: 68°0 C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C.,2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v); Molecular Probes) dissolved in 1×TE and 0.5 μl of undiluted PCR product into each well of an opaque fluorimeter plate (Corning Science Products Cornungny) and allowing the DNA to bind to the reagent. The plate was scanned in a Fluoroskan II (Labsystems Oy Helsinki, Fla.) to measure the fluorescence of the sample and to quantify the concentration of DNA. A 5 μl to 10 μl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGAR-ACE (Promega). Extended fragments were religated using T4 ligase (England Biolabs, Beverly Mass.) into pUC 18 vector (Amersham Pharmacia Biotech), treated with Pfu DNA polymerase (Stratagene) to fill-in restriction site overhangs, and transformed into competent E. coli cells. Transformed cells were selected on antibiotic-containing media, and individual colonies were picked and cultured overnight at 37° C. in 384-well plates in LB/2×carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystem).

In like manner, the nucleotide sequence of SEQ ID NO:1 is used to obtain regulatory sequences using the procedure above, oligonucleotides designed for outward extension, and an appropriate genomic library.

VI Labeling of Probes and Hybridization Analyses

Polynucleotide sequences are isolated from a biological source and applied to a solid matrix (a blot) suitable for standard nucleic acid hybridization protocols by one of the following methods. A mixture of target nucleic acids, a restriction digest of genomic DNA, is fractionated by electrophoresis through an 0.7% agarose gel in 2× TAE [Tris-acetate-ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a blot by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 (Amersham Pharmacia Biotech). Purified target nucleic acids are robotically arrayed onto a glass microscope slide (Corning Science Products, Corning N.Y.). The slide was previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probe sequences are made from mRNA templates. Five micrograms of mRNA is mixed with 1 μg random primer (Life Technologies), incubated at 70° C. for 10 minutes, and lyophilized. The lyophilized sample is resuspended in 50 μl of 1× first strand buffer (cDNA Synthesis systems; Life Technologies) containing a dNTP mix, [$\alpha$-$^{32}$P] dCTP, dithiothreitol, and MMLV reverse transcriptase (Stratagene), and incubated at 42° C. for 1–2 hours. After incubation, the probe is diluted with 42 μl $dH_2O$, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionuclide, [$^{32}$P]dCTP.

Hybridization is carried out at 65° C. in a hybridization buffer containing 0.5 M sodium phosphate (pH 7.2), 7% SDS, and 1 mM EDTA. After the blot is incubated in hybridization buffer at 65° C. for at least 2 hours, the buffer is replaced with 10 ml of fresh buffer containing the probe sequences. After incubation at 65° C. for 18 hours, the hybridization buffer is removed, and the blot is washed sequentially under increasingly stringent conditions, up to 40 mM sodium phosphate, 1% SDS, 1 mM EDTA at 65° C. To detect signal produced by a radiolabeled probe hybridized on a membrane, the blot is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the blot is examined by confocal laser microscopy, and images are collected and analyzed using GEMTOOLS gene expression analysis software (Incyte Pharmaceuticals).

VII Complementary Polynucleotides

Sequences complementary to the polynucleotide, or a fragment thereof, are used to detect, decrease, or inhibit gene expression. Although use of oligonucleotides comprising from about 15 to about 30 base pairs is described, essentially the same procedure is used with with larger or smaller fragments or their derivatives (PNAs). Appropriate oligonucleotides are designed using OLIGO 4.06 software (National Biosciences) and SEQ ID NO:1 or its fragments, SEQ ID NO:3–9. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subdloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The nonessential polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (supra, unit 16). Purified mammalian protein obtained by these methods can be used directly in the following activity assay.

IX Functional Assays

Protein function is assessed by expressing the sequences encoding TFRP at physiologically elevated levels in mammalian cell culture. The polynucleotide is subcloned into pCMV SPORT vector (Life Technologies), which contains the strong cytomegalovirus promoter, and 5–10 μg of the vector is transformed into a endothelial or hematopoietic human cell line using electroporation. An additional 1–2 μg of a plasmid containing sequence encoding CD64-GFP (Clontech) is co-transformed to provide an fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either human IgG or antibody against CD64 (DYNAL, Lake Success N.Y.). mRNA is purified from the cells and analyzed by hybridization techniques.

X Production of TFRP Specific Antibodies

TFRP substantially purified using polyacrylamide gel electrophoresis is used to immunize rabbits and to produce antibodies using standard protocols.

Alternatively, the amino acid sequence of TFRP is analyzed using LASERGENE software (DNASTAR) to determine regions of high immunogenicity. An immunogenic epitope such as those near the C-terminus or in hydrophilic regions is selected, synthesized, and used to raise antibodies by means known to those of skill in the art.

Typically, epitopes of about 15 residues in length are produced using an ABI 431A Peptide synthesizer (PE Biosystem) using Fmoc-chemistry and coupled to KLH (Sigma-Aldrich) by reaction with N-maleimidobenzoyl-N-hydroxysuccinimide ester to increase immunogenicity. Rabbits are immunized with the epitope-KLH complex in complete Freund's adjuvant. Immunizations are repeated at intervals thereafter in incomplete Freund's adjuvant. After a sufficient period of time, antisera are drawn and tested for antipeptide activity. Testing involves binding the peptide to plastic, blocking with 1% bovine serum albumin, reacting with rabbit antisera, washing, and reacting with radioiodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the column is eluted using a buffer of pH 2–3 or a high concentration of urea or thiocyanate ion to disrupt antibody/protein binding, and the protein is collected.

XII Screening Molecules for Specific Binding with the Polynucleotide or Protein

The nucleic acid sequence, or fragments thereof, or the protein, or portions thereof, are labeled with $^{32}$P-dCTP, Cy3-dCTP, Cy5-dCTP (Amersham Pharmacia Biotech), or BIODIPY or FITC (Molecular Probes, Eugene Oreg.), respectively. Libraries of candidate molecules previously arranged on a suitable substrate are incubated in the presence of labeled nucleic acid sequence or protein. After incubation for a suitable period under appropriate conditions for the nucleic acid sequence or protein, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XIII Demonstration of Protein Activity

TFRP activity is measured by its ability to modulate transcription of a reporter gene. The assay entails the use of a reporter gene construct that consists of a transcription factor response element fused upstream to sequences encoding the *E. coli* β-galactosidase enzyme (LacZ). Sequences encoding TFRP are subcloned into a mammalian expression vector containing a strong promoter that drives high levels of cDNA expression. Vectors of choice include PCMV SPORT (Life Technologies) and PCR 3.1 (Invitrogen, Carlsbad, Calif.), both of which contain the cytomegalovirus promoter. The recombinant vector and reporter gene construct of co-transfected into a human cell line, preferably of endothelial or hematopoietic origin, using either liposome formulations or electroporation. The amount of β galactosidase enzyme activity associated with TFRP transfected cells, relative to control cells transfected with the reporter construct alone, is proportional to the amount of transcription modulated by the TFRP gene product.

TABLE 1

| SEQ ID NO | Clone Number | Nucleotide Length | Source | Library | Coverage | Percent Identity |
|---|---|---|---|---|---|---|
| 3 | 1416935F6 | 457 | *Homo sapiens* | BRAINOT12 | 1–458 | |
| 4 | 2481857F6 | 679 | *Homo sapiens* | SMCANOT01 | 343–1042 | |
| 5 | 2667068H1 | 263 | *Homo sapiens* | NPOLNOT01 | 824–1087 | |
| 6 | 3550644H1 | 291 | *Homo sapiens* | SYNONOT01 | 941–1231 | |
| 7 | SBFA02969F1 | 597 | *Homo sapiens* | mixed | 1124–1722 | |
| 8 | 1412996F6 | 493 | *Homo sapiens* | BRAINOT12 | 1238–1732 | |
| 9 | 1666914F6 | 494 | *Homo sapiens* | BMARNOT03 | 1688–2193 | |
| 10 | 700180450H1 | 296 | *Rattus norvegicus* | RALUNOT01 | 74–369 | 57 |
| 11 | 700396307H1 | 290 | *Rattus norvegicus* | RAHTNOT01 | 1747–2039 | 82 |
| 12 | 700124637H1 | 261 | *Rattus norvegicus* | RABHNOT01 | 1890–2152 | 82 |
| 13 | 700505292H1 | 264 | *Rattus norvegicus* | RALINON07 | 1969–2233 | 78 |
| 14 | 701385411H1 | 107 | *Mus musculus* | MOAPUNT01 | 1680–1786 | 85 |
| 15 | 700706387H1 | 111 | *Macaca fascicularis* | MNBFNOT01 | 1226–1336 | 99 |
| 16 | 700706487H1 | 310 | *Macaca fascicularis* | MNBFNOT01 | 1226–1536 | 97 |

What is claimed is:

1. An isolated nucleic acid sequence encoding the amino acid sequence of SEQ ID NO:2.

2. An isolated nucleic acid sequence comprising SEQ ID NO:1.

3. An isolated nucleic acid sequence selected from the group consisting of: SEQ ID NOS:3–9.

4. The complement of the nucleic acid sequence of claim 1.

5. The complement of the nucleic acid sequence of claim 3.

6. An expression vector comprising the nucleic acid sequence of claim 1.

7. A host cell containing the expression vector of claim 6.

8. A method for producing a protein, the method comprising the steps of:

(a) culturing the host cell of claim 7 under conditions suitable for the expression of the protein; and (b) recovering the protein from the host cell culture.

9. A method for detecting a mammalian nucleic acid sequence in a sample, the method comprising the steps of:
   (a) hybridizing the nucleic acid sequence of claim 1 to at least one nucleic acid sequence in the sample, thereby forming a hybridization complex; and
   (b) detecting the hybridization complex, wherein the presence of the hybridization complex correlates with the presence of the mammalian nucleic acid sequence in the sample.

10. The method of claim 9 further comprising amplifying the nucleic acid sequence or a fragment thereof prior to hybridization.

11. A method of using a mammalian nucleic acid sequence or a fragment thereof to screen a library of molecules to identify at least one molecule which specifically binds the nucleic acid sequence, the method comprising:
   (a) providing a library of molecules,
   (b) combining the nucleic acid sequence of claim 1 with a library of molecules under conditions suitable to allow specific binding, and
   (c) detecting specific binding, thereby identifying a molecule which specifically binds the nucleic acid sequence.

12. The method of claim 11 wherein the library is selected from the group consisting of: DNA molecules, RNA molecules, PNAs, peptides, and proteins.

\* \* \* \* \*

SEQUENCE LISTING

<160> NUMBER OF SEQ ID NOS: 17

<210> SEQ ID NO 1
<211> LENGTH: 2262
<212> TYPE: DNA
<213> ORGANISM: Homo sapiens
<220> FEATURE:
<221> NAME/KEY: unsure
<222> LOCATION: 2204, 2229
<223> OTHER INFORMATION: a or g or c or t, unknown, or other
<220> FEATURE: -
<223> OTHER INFORMATION: 2667068

<400> SEQUENCE: 1

```
ggagagttgt gcgccggtcc ctgggcctga gctccggctc cggctggggc gcctgcgatg      60
tctcaagatg gcggagctgg gcgaattaaa gcacatggtg atgagtttcc gggtgtctga     120
gctccaggtg cttcttggct ttgctggccg gaacaagagt ggacggaagc acgagctcct     180
ggccaaggct ctgcacctcc tgaagtccag ctgtgcccct agtgtccaga tgaagatcaa     240
agagctttac cgacgacgct ttccccggaa gaccctgggg ccctctgatc tctcccttct     300
```

```
ctctttgccc cctggcacct ctcctgtagg ctcccctggt cctctagctc ccattccccc      360
aacgctgttg gcccctggca ccctgctggg ccccaagcgt gaggtggaca tgcacccccc      420
tctgccccag cctgtgcacc ctgatgtcac catgaaacca ttgcccttct atgaagtcta      480
tggggagctc atccggccca ccaccccttgc atccacttct agccagcggt ttgaggaagc     540
gcactttacc tttgccctca cacccccagca agtgcagcag attcttacat ccagagaggt    600
tctgccagga gccaaatgtg attataccat acaggtgcag ctaaggttct gtctctgtga      660
gaccagctgc ccccaggaag attattttcc ccccaacctc tttgtcaagg tcaatgggaa      720
actgtgcccc ctgccggggtt accttccccc aaccaagaat ggggccgagc caagaggcc     780
cagccgcccc atcaacatca cacccctggc tcgactctca gccactgttc ccaacaccat      840
tgtggtcaat tggtcatctg agttcggacg gaattactcc ttgtctgtgt acctggtgag      900
gcagttgact gcaggaaccc ttctacaaaa actcagagca aagggtatcc ggaacccaga      960
ccactcgcgg gcactgatca aggagaaatt gactgctgac cctgacagtg aggtggccac     1020
tacaagtctc cgggtgtcac tcatgtgccc gctaggaag atgcgcctga ctgtcccttg     1080
tcgtgccctc acctgcgccc acctgcagag cttcgatgct gcccttate tacagatgaa     1140
tgagaagaag cctacatgga catgtcctgt gtgtgacaag aaggctccct atgaatctct    1200
tatcattgat ggtttatttta tggagattct tagttcctgt tcagattgtg atgagatcca     1260
attcatggaa gatggatcct ggtgcccaat gaaacccaag aaggaggcat ctgaggtttg      1320
cccccccgcca gggtatgggc tggatggcct ccagtacagc ccagtccagg ggggagatcc     1380
atcagagaat aagaagaagg tcgaagttat tgacttgaca atagaaagct catcagatga     1440
ggaggatctg ccccctacca agaagcactg ttctgtcacc tcagctgcca tcccggccct    1500
acctggaagc aaaggagtcc tgacatctgg ccaccagcca cctcggtgc taaggagccc     1560
tgctatgggc acgttgggtg gggatttcct gtccagtctc ccactacatg agtacccacc      1620
tgccttccca ctgggagccg acatccaagg tttagattta tttttcattttc ttcagacaga     1680
gagtcagcac tatggccccct ctgtcatcac ctcactagat gaacaggatg cccttggcca     1740
cttcttccag taccgaggga cccccttctca ctttctgggc ccactggccc ccacgctggg     1800
gagctcccac tgcagcgcca ctccggcgcc ccctcctggc cgtgtcagca gcattgtggc     1860
ccctgggggg gccttgaggg agggggcatgg aggaccctg ccctcaggtc cctctttgac    1920
tggctgtcgg tcagacatca tttccctgga ctgagttccc tggattatgg aaacttcgct   1980
gtccccaac actgagcaag tatgctgtgg agtcccaacc ccagctactc tgatccctct     2040
gggggctctg gccaagggcc agacagacct tcacagatgc ctactttttgg cctcatctct   2100
gcctgacaag gccagcaccc aaagggttaa tatttaacct cttttttaag gacactgggg     2160
tctgtctcct ggaatgttct ttagatggtg gcacattcct ttgnggtatg ttaacctagg    2220
cactgggang caaatgggga ttgtatgtga gctaggagaa gg                        2262
```

<210> SEQ ID NO 2
<211> LENGTH: 628
<212> TYPE: PRT
<213> ORGANISM: Homo sapiens
<220> FEATURE: -
<223> OTHER INFORMATION: 2667068

<400> SEQUENCE: 2

```
Met Ala Glu Leu Gly Glu Leu Lys His Met Val Met Ser Phe Arg
 1               5                  10                  15
```

-continued

```
Val Ser Glu Leu Gln Val Leu Leu Gly Phe Ala Gly Arg Asn Lys
             20                  25                  30

Ser Gly Arg Lys His Glu Leu Leu Ala Lys Ala Leu His Leu Leu
             35                  40                  45

Lys Ser Ser Cys Ala Pro Ser Val Gln Met Lys Ile Lys Glu Leu
             50                  55                  60

Tyr Arg Arg Arg Phe Pro Arg Lys Thr Leu Gly Pro Ser Asp Leu
             65                  70                  75

Ser Leu Leu Ser Leu Pro Pro Gly Thr Ser Pro Val Gly Ser Pro
             80                  85                  90

Gly Pro Leu Ala Pro Ile Pro Pro Thr Leu Leu Ala Pro Gly Thr
             95                 100                 105

Leu Leu Gly Pro Lys Arg Glu Val Asp Met His Pro Pro Leu Pro
            110                 115                 120

Gln Pro Val His Pro Asp Val Thr Met Lys Pro Leu Pro Phe Tyr
            125                 130                 135

Glu Val Tyr Gly Glu Leu Ile Arg Pro Thr Thr Leu Ala Ser Thr
            140                 145                 150

Ser Ser Gln Arg Phe Glu Glu Ala His Phe Thr Phe Ala Leu Thr
            155                 160                 165

Pro Gln Gln Val Gln Gln Ile Leu Thr Ser Arg Glu Val Leu Pro
            170                 175                 180

Gly Ala Lys Cys Asp Tyr Thr Ile Gln Val Gln Leu Arg Phe Cys
            185                 190                 195

Leu Cys Glu Thr Ser Cys Pro Gln Glu Asp Tyr Phe Pro Pro Asn
            200                 205                 210

Leu Phe Val Lys Val Asn Gly Lys Leu Cys Pro Leu Pro Gly Tyr
            215                 220                 225

Leu Pro Pro Thr Lys Asn Gly Ala Glu Pro Lys Arg Pro Ser Arg
            230                 235                 240

Pro Ile Asn Ile Thr Pro Leu Ala Arg Leu Ser Ala Thr Val Pro
            245                 250                 255

Asn Thr Ile Val Val Asn Trp Ser Ser Glu Phe Gly Arg Asn Tyr
            260                 265                 270

Ser Leu Ser Val Tyr Leu Val Arg Gln Leu Thr Ala Gly Thr Leu
            275                 280                 285

Leu Gln Lys Leu Arg Ala Lys Gly Ile Arg Asn Pro Asp His Ser
            290                 295                 300

Arg Ala Leu Ile Lys Glu Lys Leu Thr Ala Asp Pro Asp Ser Glu
            305                 310                 315

Val Ala Thr Thr Ser Leu Arg Val Ser Leu Met Cys Pro Leu Gly
            320                 325                 330

Lys Met Arg Leu Thr Val Pro Cys Arg Ala Leu Thr Cys Ala His
            335                 340                 345

Leu Gln Ser Phe Asp Ala Ala Leu Tyr Leu Gln Met Asn Glu Lys
            350                 355                 360

Lys Pro Thr Trp Thr Cys Pro Val Cys Asp Lys Lys Ala Pro Tyr
            365                 370                 375

Glu Ser Leu Ile Ile Asp Gly Leu Phe Met Glu Ile Leu Ser Ser
            380                 385                 390

Cys Ser Asp Cys Asp Glu Ile Gln Phe Met Glu Asp Gly Ser Trp
            395                 400                 405
```

```
Cys Pro Met Lys Pro Lys Lys Glu Ala Ser Glu Val Cys Pro Pro
            410                 415                 420

Pro Gly Tyr Gly Leu Asp Gly Leu Gln Tyr Ser Pro Val Gln Gly
            425                 430                 435

Gly Asp Pro Ser Glu Asn Lys Lys Val Glu Val Ile Asp Leu
            440                 445                 450

Thr Ile Glu Ser Ser Asp Glu Glu Asp Leu Pro Pro Thr Lys
            455                 460                 465

Lys His Cys Ser Val Thr Ser Ala Ala Ile Pro Ala Leu Pro Gly
            470                 475                 480

Ser Lys Gly Val Leu Thr Ser Gly His Gln Pro Ser Ser Val Leu
            485                 490                 495

Arg Ser Pro Ala Met Gly Thr Leu Gly Gly Asp Phe Leu Ser Ser
            500                 505                 510

Leu Pro Leu His Glu Tyr Pro Pro Ala Phe Pro Leu Gly Ala Asp
            515                 520                 525

Ile Gln Gly Leu Asp Leu Phe Ser Phe Leu Gln Thr Glu Ser Gln
            530                 535                 540

His Tyr Gly Pro Ser Val Ile Thr Ser Leu Asp Glu Gln Asp Ala
            545                 550                 555

Leu Gly His Phe Phe Gln Tyr Arg Gly Thr Pro Ser His Phe Leu
            560                 565                 570

Gly Pro Leu Ala Pro Thr Leu Gly Ser Ser His Cys Ser Ala Thr
            575                 580                 585

Pro Ala Pro Pro Pro Gly Arg Val Ser Ser Ile Val Ala Pro Gly
            590                 595                 600

Gly Ala Leu Arg Glu Gly His Gly Gly Pro Leu Pro Ser Gly Pro
            605                 610                 615

Ser Leu Thr Gly Cys Arg Ser Asp Ile Ile Ser Leu Asp
            620                 625

<210> SEQ ID NO 3
<211> LENGTH: 548
<212> TYPE: DNA
<213> ORGANISM: Homo sapiens
<220> FEATURE:
<221> NAME/KEY: unsure
<222> LOCATION: 76, 231, 303, 306, 307, (309)...(312), 324, 331, 332,
      365,
<221> NAME/KEY: unsure
<222> LOCATION: 379, 399, 406, 409, 415, 419, 425, 436, 450, 474, 498,
      501,
<221> NAME/KEY: unsure
<222> LOCATION: 504, 516, 529
<223> OTHER INFORMATION: a or g or c or t, unknown, or other
<220> FEATURE: -
<223> OTHER INFORMATION: 1416935F6

<400> SEQUENCE: 3
ggagagttgt gcgccggtcc ctgggcctga gctccggctc cggctggggc gcctgcgatg    60
tctcaagatg gcggantggg cgaattaaag cacatggtga tgagtttccg ggtgtctgag   120
ctccaggtgc ttcttggctt tgctggccgg aacaagagtg acggaagca cgagctcctg    180 gccaaggctc tgcacctcct gaagtccagc tgtgcccta gtgtccagat naagatcaaa    240
gagctttacc gacggacgct tccccggaa gaccctgggg ccctctgatc tcccttct     300 ctnttnnann nntggcaact ctcntgtagg nngccctggt cctctagctc ccattccccc   360
aacgntgttg gccccctggna ccctgctggg ccccaagcnt gaggtngana tgcancccnc   420
```

```
tctgntccag cctgtngaac ctgatgtcan catgaaacca ttgcccttct atgnagtcta      480
tggggagctc atccggcnga ncanccttgc attcanttgt aagcaagang tttgaggaag      540
cgcaattt                                                              548
```

<210> SEQ ID NO 4
<211> LENGTH: 679
<212> TYPE: DNA
<213> ORGANISM: Homo sapiens
<220> FEATURE:
<221> NAME/KEY: unsure
<222> LOCATION: 163, 202, 219, 221, 256, 364, 386, 393, 409, 421, 423,
      428,
<221> NAME/KEY: unsure
<222> LOCATION: 436, 438, 451, 473, 478, 494, 495, 503, 504, 514, 515,
      527,
<221> NAME/KEY: unsure
<222> LOCATION: 529, 536, 541, 563, 566, 594, 602, 621, 622, 637, 639,
      641,
<221> NAME/KEY: unsure
<222> LOCATION: 647, 651, 655, 658, 659, 663, 672
<223> OTHER INFORMATION: a or g or c or t, unknown, or other
<220> FEATURE: -
<223> OTHER INFORMATION: 2481857F6

<400> SEQUENCE: 4

```
ctctagctcc cattcccca acgctgttgg ccctggcac cctgctgggc cccaagcgtg        60
aggtggacat gcaccccct ctgccccagc ctgtgcaccc tgatgtcacc atgaaaccat      120 tgccttcta tgaagtctat ggggagctca tccggcccac canccttgca tccacttcta     180
gccagcggtt tgaggaagcg cntttaccct tgccctcana ncccagcaag tgcagcagat     240
tcttacatcc agaganggtc tgccaggagc caaatgtgat tatacataca ggtgcagtaa     300
ggttctgtct ctgtgagacc agtgccccag gaagattatt ttccccccaa cctcttggca     360
aggnaatggg gaactgtgcc cctgcngggg tanctttccc ccaaccaana tggggcgaa      420 ncnaagangc caagcngncc atcaacatta naccctgggt cgaatttaag cantgttnca     480
aaaacaattg tggnnattgg cannttattc gggnnggaat tatcctngnt gtgtanctgg     540
ngaggaattg atgaggaacc ttntanaaaa attgaggaaa gggttcggaa ccanacaatt     600
gnggggctgt taaggggaat nnttgtgacc tgaaatnang nggcatnaaa nttcnggnnt     660
aanattttcc cntaggaaa                                                  679
```

<210> SEQ ID NO 5
<211> LENGTH: 263
<212> TYPE: DNA
<213> ORGANISM: Homo sapiens
<220> FEATURE: -
<223> OTHER INFORMATION: 2667068H1

<400> SEQUENCE: 5

```
catatcccag accacttcca tgtgacgtcc cactggcccc caaagacgct ccacccagca       60
gcctctcagc cagagccatc tgttcctggc cttaccaact cctgggcttc ctccagcctt      120 gctgaccca tggctctggc ctcactttg tttcagtcaa ggagaaattg actgctgacc        180
ctgacagtga ggtggccact acaagtctcc gggtgtcact catgtgcccg ctagggaaga     240
tgcgcctgac tgtcccttgt cgt                                             263
```

<210> SEQ ID NO 6
<211> LENGTH: 291
<212> TYPE: DNA
<213> ORGANISM: Homo sapiens
<220> FEATURE: -

<223> OTHER INFORMATION: 3550644H1

<400> SEQUENCE: 6

| gcaaagggta tccggaaccc agaccactcg cgggcactga tcaaggagaa attgactgct | 60 |
| gaccctgaca gtgaggtggc cactacaagt ctccggtgt cactcatgtg cccgctaggg | 120 |
| aagatgcgcc tgactgtccc ttgtcgtgcc ctcacctgcg cccacctgca gagcttcgat | 180 |
| gctgcccttt atctacagat gaatgagaag aagcctacat ggacatgtcc tgtgtgtgac | 240 |
| aagaaggctc cctatgaatc tcttatcatt gatggtttat ttatggagat t | 291 |

<210> SEQ ID NO 7
<211> LENGTH: 597
<212> TYPE: DNA
<213> ORGANISM: Homo sapiens
<220> FEATURE:
<221> NAME/KEY: unsure
<222> LOCATION: 16, 19, 55, 86, 97, 110, 112, 114, 363, 498, 548
<223> OTHER INFORMATION: a or g or c or t, unknown, or other
<220> FEATURE: -
<223> OTHER INFORMATION: SBFA02969F1

<400> SEQUENCE: 7

| gccctttttc tacagntgna tgtgaagaag cctacatgga catgtcctgt gtgtnacaag | 60 |
| aaggctccct atgaatctct tatcantgat ggtttantta tggagattcn tngntcctgt | 120 |
| tcagattgtg atgagatcca attcatggaa gatggatcct ggtgcccaat gaaacccaag | 180 |
| aaggaggcat ctgaggtttg ccccccgcca gggtatgggc tggatggcct ccagtacagc | 240 |
| ccagtccagg gggagatcc atcagagaat aagaagaagg tcgaagttat tgacttgaca | 300 |
| atagaaagct catcagatga ggaggatctg ccccctacca agaagcactg ttctgtcacc | 360 |
| tcngctgcca tcccggccct acctggaagc aaaggagtcc tgacatctgg ccaccagcca | 420 |
| tcctcggtgc taaggagccc tgctatgggc acgttgggtg gggatttcct gtccagtctc | 480 |
| ccactacatg agtacccngc tgccttccca ctgggagccg acatccaagg tttagattta | 540 |
| ttttcatntc ttcagacaga gagtcagcac tatgggggga tcctctagag tcgacct | 597 |

<210> SEQ ID NO 8
<211> LENGTH: 523
<212> TYPE: DNA
<213> ORGANISM: Homo sapiens
<220> FEATURE:
<221> NAME/KEY: unsure
<222> LOCATION: 502, 520
<223> OTHER INFORMATION: a or g or c or t, unknown, or other
<220> FEATURE: -
<223> OTHER INFORMATION: 1412996F6

<400> SEQUENCE: 8

| tcctgttcag attgtgatga gatccaattc atggaagatg gatcctggtg cccaatgaaa | 60 |
| cccaagaagg aggcatctga ggtttgcccc ccgccaggta tgggctggat ggcctccagt | 120 |
| acagcccagt ccaggggga gatccatcag agaataagaa gaaggtcgaa gttattgact | 180 |
| tgacaataga aagctcatca gatgaggagg atctgccccc taccaagaag cactgttctg | 240 |
| tcacctcagc tgccatcccg gccctacctg gaagcaaagg agtcctgaca tctggccacc | 300 |
| agccatcctc ggtgctaagg agccctgcta tgggcacgtt gggtggggat tcctgtcca | 360 |
| gtctcccact acatgagtac cccacctgcc ttcccactgg ggagccgaca tccaaggttt | 420 |
| agatttattt tcatttcttc agacagagag tcagcactat gggccctctg tcatcactca | 480 |
| ctagatgaac aggatgccct tnggcacttc tttccagtan cgg | 523 |

<210> SEQ ID NO 9
<211> LENGTH: 568
<212> TYPE: DNA
<213> ORGANISM: Homo sapiens
<220> FEATURE:
<221> NAME/KEY: unsure
<222> LOCATION: 517
<223> OTHER INFORMATION: a or g or c or t, unknown, or other
<220> FEATURE: -
<223> OTHER INFORMATION: 1666914F6

<400> SEQUENCE: 9

| | | | | | |
|---|---|---|---|---|---|
| gtcagcacta | tggcccctct | gtcatcacct | cactagatga | acaggatgcc | cttggccact | 60 |
| tcttccagta | ccgagggacc | ccttctcact | ttctgggccc | actggccccc | acgctgggga | 120 |
| gctcccactg | cagcgccact | ccggcgcccc | ctcctggccg | tgtcagcagc | attgtggccc | 180 |
| ctgggggggc | cttgagggag | gggcatggag | gaccccctgcc | ctcaggtccc | tctttgactg | 240 |
| gctgtcggtc | agacatcatt | tccctggact | gagttccctg | gattatggaa | acttcgctgt | 300 |
| cccccaacac | tgagcaagta | tgctgtggag | tcccaacccc | agctatctga | tccctctggg | 360 |
| ggctctggcc | aagggcagac | agacttcaca | gatgctattt | tggctcattc | tgctgacaag | 420 |
| gcaagcacca | aaggttaata | tttaactctt | ttttaaggac | actggggtct | gtttctggaa | 480 |
| atgttcttta | gatggtggca | atttcctttg | ggtatgntaa | acctaagcaa | ttgggaagga | 540 |
| aatgggatgg | tatgtgaact | aagaaaag | | | | 568 |

<210> SEQ ID NO 10
<211> LENGTH: 296
<212> TYPE: DNA
<213> ORGANISM: Rattus norvegicus
<220> FEATURE:
<221> NAME/KEY: unsure
<222> LOCATION: 207, 217, 226, 235, 261, 274, 285, 288
<223> OTHER INFORMATION: a or g or c or t, unknown, or other
<220> FEATURE: -
<223> OTHER INFORMATION: 700180450H1

<400> SEQUENCE: 10

| | | | | | |
|---|---|---|---|---|---|
| gagctggtgg | aggccaaaaa | catggtgatg | agcttccgag | tgtcagacct | gcagatgctg | 60 |
| ctgggctttg | taggtcgtag | caagagcggg | ctgaagcatg | agctggtgac | cagggccttg | 120 |
| cagctggtgc | agtttgactg | tagcccggag | cttttcaaga | agatcaaaga | gctgtatgag | 180 |
| actcgctatg | ccaagaagag | tgcagaccccc | ggcccanagg | cgccanggcc | ctggntccct | 240 |
| ggcatacact | catgcccagg | nctccctgtc | aggncccccg | tggantancc | ctgtgt | 296 |

<210> SEQ ID NO 11
<211> LENGTH: 290
<212> TYPE: DNA
<213> ORGANISM: Rattus norvegicus
<220> FEATURE:
<221> NAME/KEY: unsure
<222> LOCATION: 195, 127, 135, 139, 149, 162, 163, 173, 182, 183
<223> OTHER INFORMATION: a or g or c or t, unknown, or other
<220> FEATURE: -
<223> OTHER INFORMATION: 700396307H1

<400> SEQUENCE: 11

| | | | | | |
|---|---|---|---|---|---|
| tccaattccg | gggaacccct | ccccacttcc | tgggcccact | ggccccacca | ttggggagct | 60 |
| ctcaccgcag | cgccactcca | gcacgcgctc | tggccgtgt | cagcagcatt | gtggctcctg | 120 |
| ggagttcctt | gagggaaggg | catggaggac | ccctgccttc | cggtccctct | ttgactggct | 180 |

```
gtcggtcaga cgtanatttc cttggactga gttatttgga ttgcaanatc aattnctant    240
ggccctacna tgagcagata annggggtt ccnaacccgg anntgctctc                290
```

```
<210> SEQ ID NO 12
<211> LENGTH: 261
<212> TYPE: DNA
<213> ORGANISM: Rattus norvegicus
<220> FEATURE: -
<223> OTHER INFORMATION: 700124637H1

<400> SEQUENCE: 12
```

```
ggaggacccc tgccttccgg tccctctttg actggctgtc ggtcagacgt catttccttg     60
gactgagtta tttggattgc aaaatcaatt tctactggcc ctagcactga gcagatacat   120
tgtgggttcc caaccctgg ctgctctgat ccctcagggg tcattggtca aaggccaggc    180
cagatcttca tggacacctg cttttggcct tatcactgcc taacaaggcc agtactcaaa   240
gggttaacat ttaacctttt g                                             261
```

```
<210> SEQ ID NO 13
<211> LENGTH: 264
<212> TYPE: DNA
<213> ORGANISM: Rattus norvegicus
<220> FEATURE: -
<223> OTHER INFORMATION: 700505292H1

<400> SEQUENCE: 13
```

```
gcaaaatcaa tttctactgg ccctagcact gagcagatac attgtgggtt cccaaccct     60 ggctgctctg atccctcagg ggtcattggt caaaggccag ccagatctt catggacacc   120 tgcttttggc cttatcactg cctaacaagg ccagtactca aagggttaac atttaacctt   180
ttgaaaaagg acattgggt ctgttttgg aatgttcttt gatgtagcac attcctttgg    240
gtagggtaac ctaggcagtg ggag                                          264
```

```
<210> SEQ ID NO 14
<211> LENGTH: 107
<212> TYPE: DNA
<213> ORGANISM: Mus musculus
<220> FEATURE: -
<223> OTHER INFORMATION: 701385411H1

<400> SEQUENCE: 14
```

```
ctctccagca ctacggccct tcagttatca cttcgctaga tgaacaggac acccttggcc    60
acttcttcca gtaccgggga accccttccc acttcctggg cccactg                 107
```

```
<210> SEQ ID NO 15
<211> LENGTH: 111
<212> TYPE: DNA
<213> ORGANISM: Macaca fascicularis
<220> FEATURE:
<221> NAME/KEY: unsure
<222> LOCATION: 77
<223> OTHER INFORMATION: a or g or c or t, unknown, or other
<220> FEATURE: -
<223> OTHER INFORMATION: 700706387H1

<400> SEQUENCE: 15
```

```
attcttagtt cctgttcaga ttgtgatgag atccaattca tggaagatgg atcctggtgc    60
ccaatgaaac ccaagangga ggcatctgag gtttgccccc cgccagggta t            111
```

```
<210> SEQ ID NO 16
<211> LENGTH: 310
```

```
<212> TYPE: DNA
<213> ORGANISM: Macaca fascicularis
<220> FEATURE: -
<223> OTHER INFORMATION: 700706487H1

<400> SEQUENCE: 16
attcttagtt cctgttcaga ttgtgatgag atccaattca tggaagatgg atcctggtgc    60
ccaatgaaac ccaagaagga ggcatctgag gtttgccccc cggccaggta tgggtggatg   120
gcctccagta cagcccagtc caggagggaa atccatcaga gaataagaag aaggtcgaag   180
ttattgactt gacaatagaa agctcatcag atgaggagga tctgcccccct accaagaagc   240
actgttctgt cacctcagct gccatcccgg ccctacctgg aagcaaagga gtcctgacgt   300
ctggccacca                                                          310

<210> SEQ ID NO 17
<211> LENGTH: 583
<212> TYPE: PRT
<213> ORGANISM: Mus musculus
<220> FEATURE: -
<223> OTHER INFORMATION: g2689028

<400> SEQUENCE: 17
```

Met Val Met Ser Phe Arg Val Ser Glu Leu Gln Val Leu Leu Gly
  1               5                  10                  15

Phe Ala Gly Arg Asn Lys Ser Gly Arg Lys His Glu Leu Leu Ala
                 20                  25                  30

Lys Ala Leu His Leu Leu Lys Ser Ser Cys Ala Pro Ser Val Gln
                 35                  40                  45

Met Lys Ile Lys Glu Leu Tyr Arg Arg Phe Pro Arg Lys Thr
             50                  55                  60

Leu Gly Pro Ser Asp Leu Ser Leu Leu Ser Leu Pro Pro Gly Thr
             65                  70                  75

Ser Pro Pro Val His Pro Asp Val Thr Met Lys Pro Leu Pro Phe
             80                  85                  90

Tyr Glu Val Tyr Gly Glu Leu Ile Arg Pro Thr Thr Leu Ala Ser
             95                 100                 105

Thr Ser Ser Gln Arg Phe Glu Glu Ala His Phe Thr Phe Ala Leu
            110                 115                 120

Thr Pro Gln Gln Leu Gln Gln Ile Leu Thr Ser Arg Glu Val Leu
            125                 130                 135

Pro Gly Ala Lys Cys Asp Tyr Thr Ile Gln Val Gln Leu Arg Phe
            140                 145                 150

Cys Leu Cys Glu Thr Ser Cys Pro Gln Glu Asp Tyr Phe Pro Pro
            155                 160                 165

Asn Leu Phe Val Lys Val Asn Gly Lys Leu Cys Pro Leu Pro Gly
            170                 175                 180

Tyr Leu Pro Pro Thr Lys Asn Gly Ala Glu Pro Arg Gly Pro Ala
            185                 190                 195

Val Arg Ser Thr Ser His Pro Trp Leu Asp Ser Gln Pro Leu Ser
            200                 205                 210

Pro Thr Pro Ser Leu Leu Ile Gly His Leu Ser Leu Asp Gly Ile
            215                 220                 225

Thr Pro Cys Pro Cys Leu Val Arg Gln Leu Thr Ala Gly Thr Leu
            230                 235                 240

Leu Gln Lys Leu Arg Ala Lys Gly Ile Arg Asn Pro Asp His Ser
            245                 250                 255

-continued

```
Arg Ala Leu Ile Lys Glu Lys Leu Thr Ala Asp Pro Asp Ser Glu
            260                 265                 270
Val Ala Thr Thr Ser Leu Pro Gly Val Thr His Val Pro Ala Arg
            275                 280                 285
Lys Met Arg Leu Thr Val Pro Cys Arg Ala Leu Thr Cys Ala His
            290                 295                 300
Leu Gln Ser Phe Asp Ala Ala Leu Tyr Leu Gln Met Asn Glu Lys
            305                 310                 315
Lys Pro Thr Trp Thr Cys Pro Val Cys Asp Lys Lys Ala Pro Tyr
            320                 325                 330
Glu Ser Leu Ile Ile Asp Gly Leu Phe Met Glu Ile Leu Asn Ser
            335                 340                 345
Cys Ser Asp Cys Asp Glu Ile Gln Phe Met Glu Asp Gly Ser Trp
            350                 355                 360
Cys Pro Met Lys Pro Lys Lys Glu Ala Ser Glu Val Cys Pro Pro
            365                 370                 375
Pro Gly Tyr Gly Leu Asp Gly Leu Gln Tyr Ser Ala Val Gln Glu
            380                 385                 390
Gly Ile Gln Pro Glu Ser Lys Lys Arg Val Glu Val Ile Asp Leu
            395                 400                 405
Thr Ile Glu Ser Ser Ser Asp Glu Glu Asp Leu Pro Pro Thr Lys
            410                 415                 420
Lys His Cys Pro Val Thr Ser Ala Ala Ile Pro Ala Leu Pro Gly
            425                 430                 435
Ser Lys Gly Ala Leu Thr Ser Gly His Gln Pro Ser Ser Val Leu
            440                 445                 450
Arg Ser Pro Ala Met Gly Thr Leu Gly Ser Asp Phe Leu Ser Ser
            455                 460                 465
Leu Pro Val His Glu Tyr Pro Pro Ala Phe Pro Leu Gly Ala Asp
            470                 475                 480
Ile Gln Gly Leu Asp Leu Phe Ser Phe Leu Gln Thr Glu Ser Gln
            485                 490                 495
Gln Tyr Gly Pro Ser Val Ile Ile Ser Leu Asp Glu Gln Asp Thr
            500                 505                 510
Leu Gly His Phe Phe Gln Tyr Arg Gly Thr Pro Ser His Phe Leu
            515                 520                 525
Gly Pro Leu Ala Pro Thr Leu Gly Ser Cys His Gly Ser Ser Thr
            530                 535                 540
Pro Ala Pro Pro Pro Gly Arg Val Ser Ser Ile Val Ala Pro Gly
            545                 550                 555
Ser Ser Leu Arg Glu Gly His Gly Gly Pro Leu Pro Ser Gly Pro
            560                 565                 570
Ser Leu Thr Gly Cys Arg Ser Asp Val Ile Ser Leu Asp
            575                 580
```